United States Patent [19]

Jessel, Jr. et al.

[11] Plant 4,978

[45] Jan. 25, 1983

[54] CHRYSANTHEMUM PLANT

[75] Inventors: Walter H. Jessel, Jr., Fremont; William E. Duffett, Salinas, both of Calif.

[73] Assignee: Yoder Brothers, Inc., Barberton, Ohio

[21] Appl. No.: 175,754

[22] Filed: Aug. 5, 1980

[51] Int. Cl.[3] ..... A01H 5/00

[52] U.S. Cl. ..... Plt./78

[58] Field of Search ..... Plt./78

*Primary Examiner*—James R. Feyrer

*Attorney, Agent, or Firm*—Schwartz, Jeffery, Schwaab, Mack, Blumenthal & Koch

[57] ABSTRACT

A chrysanthemum plant known by the cultivar name Klondike and particularly characterized as to uniqueness by the combined characteristics of flat capitulum form; decorative capitulum type; dark yellow ray floret color; diameter across face of capitulum ranging from 95 to 110 mm. at maturity; uniform nine week photoperiodic flowering response to short days; tall plant height when grown as a pinched spray pot; and semi-spreading branching pattern.

3 Drawing Figures

1

The present invention comprises a new and distinct cultivar of *Chrysanthemum morifolium*, Ramat., hereinafter referred to by the cultivar name Klondike.

Klondike is a product of a planned breeding program which had the objective of creating new chrysanthemum cultivars with decorative capitulum type, with yellow ray floret color, with eight or nine week flowering response, and with the ability to produce commercially acceptable quality in year-round pot mum programs. Such traits in combination were not present in previously available commercial cultivars.

Klondike was originated from a hybridization made in a controlled breeding program in Barberton, Ohio in 1974. The female parent was an unnamed yellow decorative seedling (#70048004) originated by the present inventors from a hybridization of Mandalay (unpatented; commercially available). and Sunstar (unpatented; commercially available). The male parent of Klondike was an unnamed yellow decorative seedling (#70031002) originated by the present inventors from a hybridization of two unnamed seedlings (#67492008 and #67491010).

Klondike was discovered and selected as one flowering plant within the progeny of the stated cross by Walter H. Jessel, Jr. and William E. Duffett on Nov. 18, 1975 in a controlled environment in Barberton, Ohio.

The first act of asexual reproduction of Klondike was accomplished when vegetative cuttings were taken from the initial selection in February 1976 in a controlled environment in Barberton, Ohio, by a technician working under formulations established and supervised by Walter H. Jessel, Jr. and William E. Duffett. Horticultural examination of selected units initiated Nov. 7, 1977 has demonstrated that the combination of characteristics as herein disclosed for Klondike are firmly fixed and are retained through successive generations of asexual reproduction.

Klondike has not been observed under all possible environmental conditions. The phenotype may vary significantly with variations in environment such as temperature, light intensity, and daylength. The observations, measurements, and comparisons describe plants grown in Barberton, Ohio and in Salinas, Calif. under greenhouse conditions which approximate those generally used in commercial practice.

2

The following traits have been repeatedly observed and are determined to be basic characteristics of Klondike which in combination distinguish this chrysanthemum as a new and distinct cultivar:

(1) Flat capitulum form;

(2) Decorative capitulum type;

(3) Dark yellow ray floret color, with minimal color oxidation;

(4) Diameter across face of capitulum ranging from 96 to 110 mm. at maturity;

(5) Uniform nine week photoperiodic flowering response to short days;

(6) Tall plant height (requiring 1–2 long day weeks prior to pinch and short days, and two applications 2500 ppm B-9 SP 7 to 14 days after the beginning of short days to attain a flowered plant height of 30 to 45 cm.); and (7) Semi-spreading branching pattern.

The accompanying photographic drawings show typical inflorescence and foliage characteristics of Klondike, with the colors being as nearly true as possible with illustrations of this type. Sheet 1 is a color photograph of a specimen plant of Klondike. Sheet 2 is a black and white photograph showing three views of the inflorescence of Klondike. Sheet 3 is a black and white photograph of the foliage of Klondike at three stages of growth.

Of the many commercial cultivars known to the present inventors, the most similar in comparison to Klondike is Tip, disclosed in U.S. Plant Pat. No. 3,867. Reference is made to attached Chart A which compares certain characteristics of Klondike to those same characteristics of Tip. In general comparison to Tip, Klondike has lighter ray floret color, longer form retention, smaller diameter across face of capitulum, and longer flowering response period. The capitulum form, capitulum type, branching pattern, and plant height of Klondike are similar to those same characteristics of Tip.

In the following description color references are made to A Limit Color Cascade, by the Munsell Company, 1972 edition. The color values were determined between 8:30 and 9:00 A.M. on Apr. 29, 1980 under 125 foot-candle light intensity at Salinas, Calif.

CLASSIFICATION

Botanical: *Chrysanthemum morifolium,* Ramat., cv Klondike.

Commercial: Pinched disbudded decorative pot plant.

I. INFLORESCENCE

A. Capitulum:

*Form.*—Flat.

*Type.*—Decorative.

*Diameter across face.*—95 to 110 mm.

B. Corolla of ray florets:

*Color (general tonality from a distance of three meters).*—Dark yellow 27-6 to 27-4.

*Color (abaxial).*—27-6 oxidizing to 27-3.

*Color (adaxial).*—27-4 to 27-2.

C. Reproductive organs:

*Androecium.*—Present disc florets only; scant to few; scant pollen.

*Gynoecium.*—Present both disc and ray florets; normal chrysanthemum.

II. PLANT

A. General appearance:

*Height.*—Tall (pot mum culture).

*Branching pattern.*—Semi-spreading.

B. Foliage:

*Color (abaxial).*—Between 20-15 and 20-13 with more gray.

*Color (adaxial).*—19-13 overlaid with white.

*Shape.*—Slightly lobed; slightly serrated.

CHART A

COMPARISON OF KLONDIKE AND TIP

| CULTIVAR | RAY FLORET COLOR | CAPITULUM FORM AND TYPE | BRANCHING PATTERN |
|---|---|---|---|
| KLONDIKE | Dark Yellow | Flat Decorative | Semi-spreading |
| TIP | Golden Yellow | Flat Decorative Relexing at maturity | Semi-spreading |

| CULTIVAR | DIAMETER ACROSS FACE OF CAPITULUM | PLANT HEIGHT | FLOWERING RESPONSE PERIOD |
|---|---|---|---|
| KLONDIKE | 95 to 110 mm. | Tall | 9 week |
| TIP | 135 to 140 mm. | Tall | 8 week |

COMPARISONS MADE OF PLANTS GROWN AS PINCHED DISBUDDED PLANTS GROWN IN BARBERTON, OHIO AND IN SALINAS, CALIFORNIA.

We claim:

1. A new and distinct cultivar of *Chrysanthemum morifolium,* Ramat., plant known by the cultivar name Klondike, as described and illustrated, and particularly characterized as to uniqueness by the combined characteristics of flat capitulum form; decorative capitulum type; dark yellow ray floret color; diameter across face of capitulum ranging from 95 to 110 mm. at maturity; uniform nine week flowering response; tall plant height; and semi-spreading branching pattern.

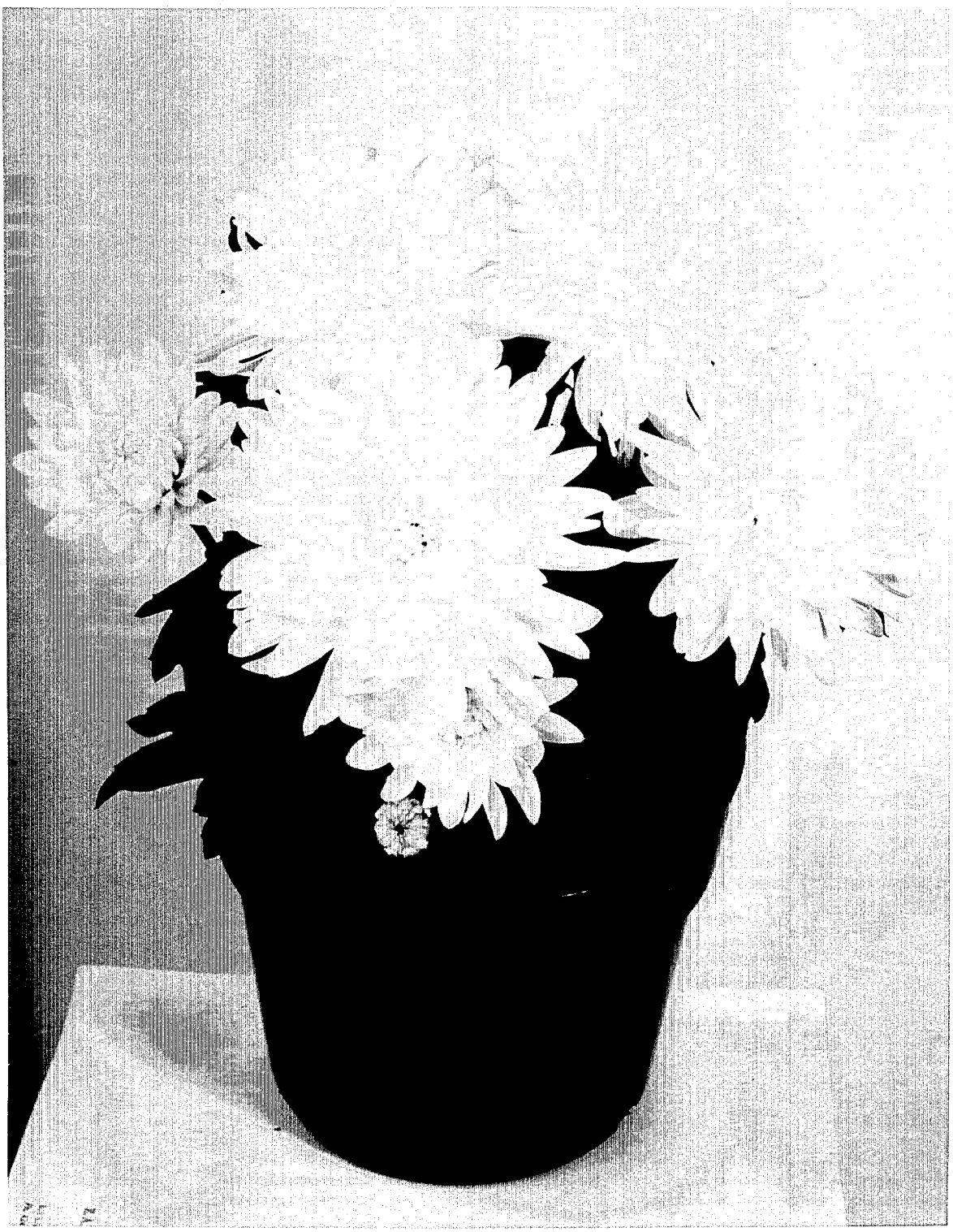

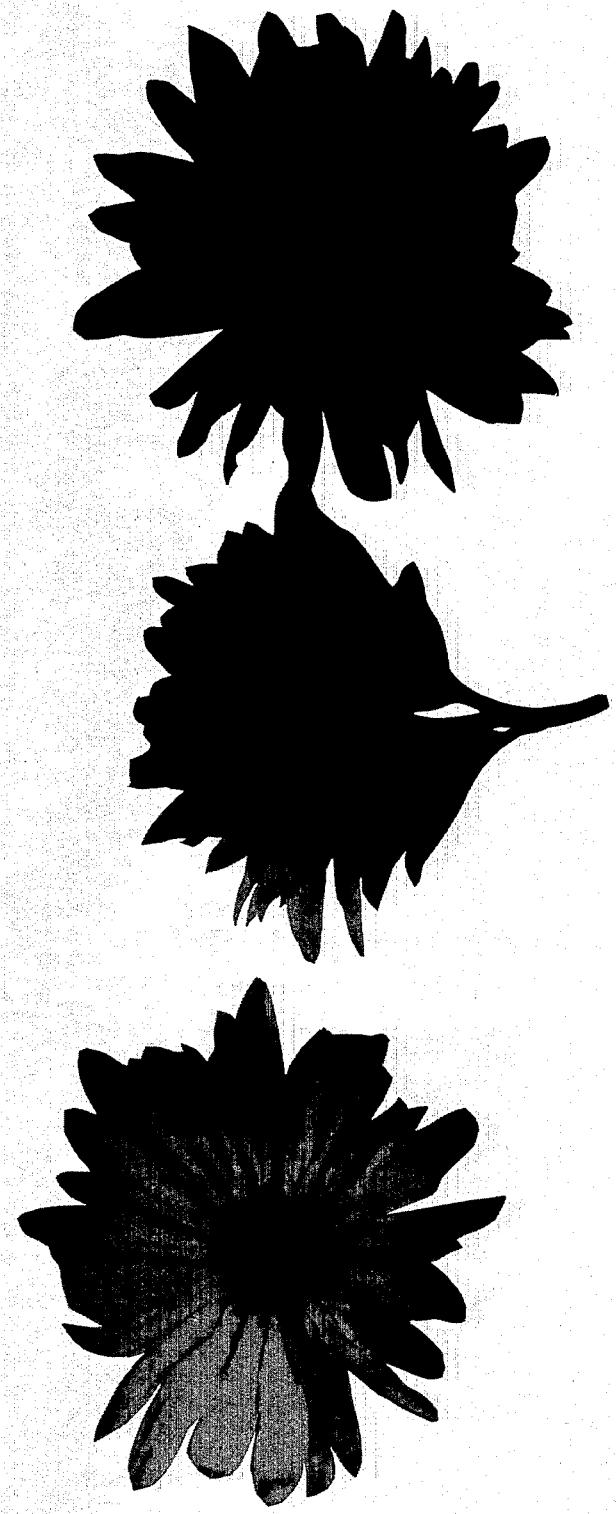

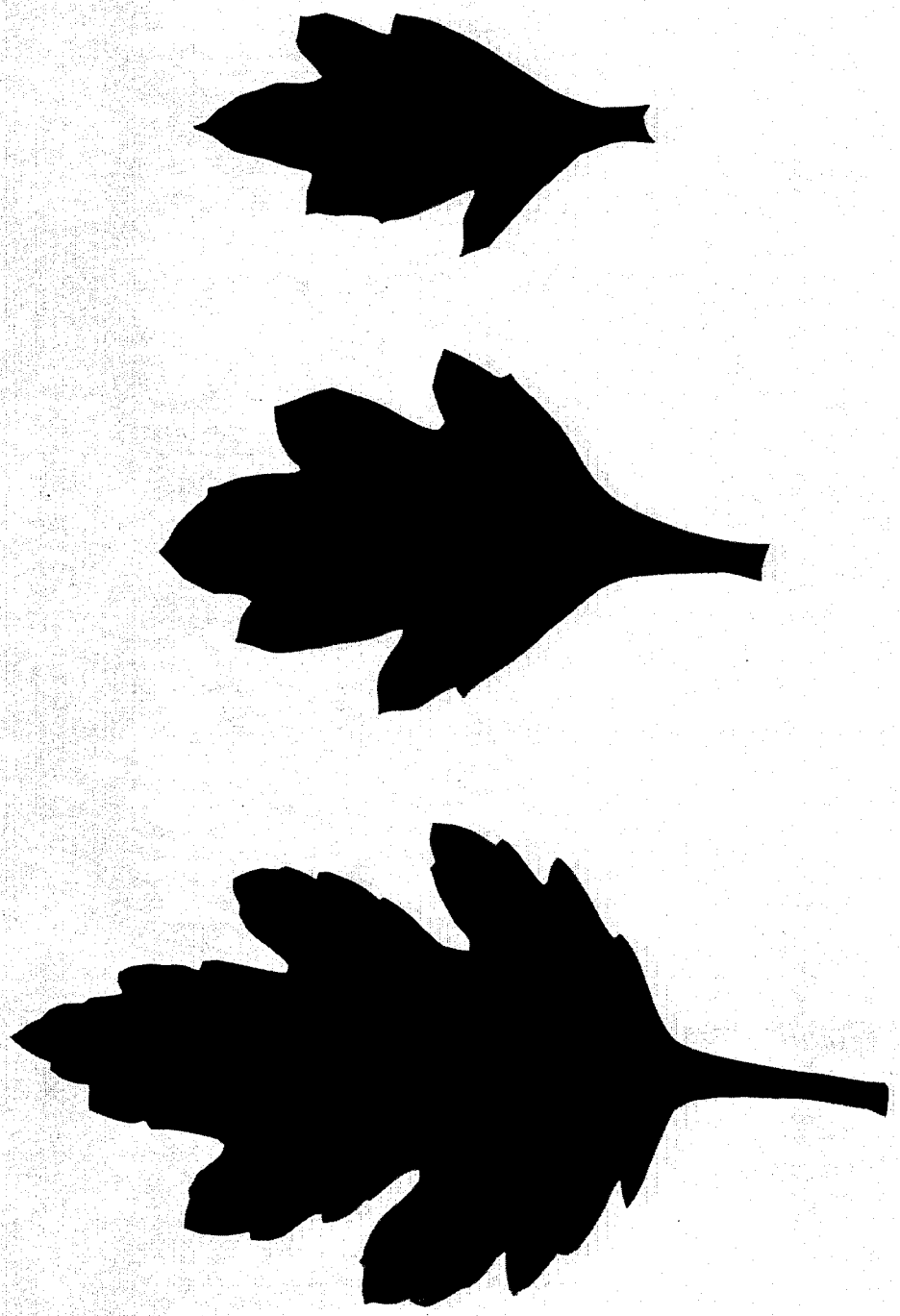

* * * * *